(12) United States Patent
Rao et al.

(10) Patent No.: US 10,308,954 B2
(45) Date of Patent: Jun. 4, 2019

(54) METHOD FOR THE CONTROL OF NEMATODES IN PLANTS

(71) Applicants: ICAR, New Delhi (IN); Department of Biotechnology, New Delhi (IN)

(72) Inventors: Uma Rao, New Delhi (IN); Pradeep Papolu, New Delhi (IN); Nagavara Prasad Gantasala, New Delhi (IN); Divya Kamaraju, New Delhi (IN); Prakash Banakar, New Delhi (IN); Mukesh Kumar, New Delhi (IN)

(73) Assignees: ICAR, New Delhi (IN); Department of Biotechnology, New Delhi (IN)

( * ) Notice: Subject to any disclaimer, the term of this patent is extended or adjusted under 35 U.S.C. 154(b) by 50 days.

(21) Appl. No.: 14/652,096

(22) PCT Filed: Dec. 14, 2013

(86) PCT No.: PCT/IB2013/060946
§ 371 (c)(1),
(2) Date: Jun. 12, 2015

(87) PCT Pub. No.: WO2014/091466
PCT Pub. Date: Jun. 19, 2014

(65) Prior Publication Data
US 2015/0361445 A1   Dec. 17, 2015

(30) Foreign Application Priority Data

Dec. 14, 2012  (IN) .......................... 3876/DEL/2012

(51) Int. Cl.
| | | |
|---|---|---|
| *C12N 15/82* | (2006.01) | |
| *A01N 63/02* | (2006.01) | |
| *C07K 14/575* | (2006.01) | |
| *C07K 14/435* | (2006.01) | |

(52) U.S. Cl.
CPC ......... *C12N 15/8285* (2013.01); *A01N 63/02* (2013.01); *C07K 14/4354* (2013.01); *C07K 14/575* (2013.01); *C12N 15/8218* (2013.01); *Y02A 40/164* (2018.01)

(58) Field of Classification Search
CPC ................................................ C12N 15/8285
USPC ......................................................... 800/279
See application file for complete search history.

(56) References Cited

U.S. PATENT DOCUMENTS

| | | | |
|---|---|---|---|
| 5,013,762 A | 5/1991 | Smith et al. | |
| 6,506,559 B1 | 1/2003 | Fire et al. | |
| 7,576,261 B2 * | 8/2009 | Hussey ............ | C07K 14/43563 426/615 |
| 9,790,516 B2 * | 10/2017 | Chiapelli ........... | C12N 15/8285 |
| 2003/0150017 A1 | 8/2003 | Mesa et al. | |
| 2008/0184391 A1 | 7/2008 | Subramaniam et al. | |
| 2010/0068172 A1 | 3/2010 | Van De Craen | |
| 2011/0150839 A1 | 6/2011 | Arciello et al. | |
| 2012/0030834 A1 | 2/2012 | Bradley et al. | |

FOREIGN PATENT DOCUMENTS

| | | |
|---|---|---|
| CN | 102352357 | 2/2012 |
| EP | 1799029 | 8/2014 |
| WO | 1998033906 | 8/1998 |
| WO | 2004005485 | 1/2004 |
| WO | 2010006804 | 1/2010 |
| WO | 2014091466 | 6/2014 |

OTHER PUBLICATIONS

Kimber et al. 2007, The FASEB Journal 21:1233-1243.*
Johnston et al. 2010, J. Helminthol. 84 (3), 253-265, abstract only.*
PCT; International Search Report and Written Opinion dated Oct. 7, 2014 in Application No. PCT/IB2013/060946.
PCT; International Preliminary Report on Patentability dated Apr. 21, 2015 in Application No. PCT/IB2013/060946.
Abad et al., "Genome Sequence of the Metazoan Plant-Parasitic Nematode Meloidogyne Incognita," Nature Biotechnolgy, 26, 909-915, (2008).
Brownlee et al., "Nematode Neuropeptides: Localization, Isolation and Functions," Parasitol Today, 12:9, 343-351, (1996).
Charlton, et al., "Additive effects of Plant Expressed Double-Stranded RNAs on Root-Knot Nematode Development," International Journal for Parasitology, 40:7, 855-864, (2010).
Dalzell et al., "Short Interfering RNA-Mediated Gene Silencing in Globodera Pallida and Meloidogyne Incognita Infective Stage Juveniles," International Journal for Parasitology, 40:1, 91-100, (2010).
Dalzell et al., "Non-Nematode-Derived Double-stranded RNAs Induce Profound Phenotypic Changes in Meloidogyne Incognita and Globodera Pallida Infective Juveniles," International Journal for Parasitology, 37, 1503-1516, (2009).
Day et al., "Parasite Peptides! The Structure and Function of Neuropeptides in Parasitic Worms," Peptides 20, 999-1019, (1999).
Fellowes et al., "Modulation of the Motility of the Vagina Vera of Ascaris Suum in Vitro by FMRFamide-related Peptiedes," Parasitology, 116, 277-287, (1998).
Fellowes et al., Classical Neurotransmitters in the Ovijector of i Ascaris suum\plain\f0\fs20: Localization and Modulation of Muscle Activity, Parasitology, 121, 325-336, (2000).
Geary et al., "Pharmacology of FMRFamide-Peptides in Helminths," Ann. N.Y. Academy of Science, 897, 212-227, (1999).
Kimber et al., "FMRFamide-related Peptides in Potato Cyst Nematodes," Molecular & Biochemical Parasitology, 116, 199-208. (2001).
Kimber et al., "Flp Gene Disruption in a Parasitic Nematode Reveals Motor Dysfunction and Unusual Neuronal Sensitivity to RNA Interference," Faseb Journal, 21:4, ISN: 0892-6638, 1233-1243, (2007).

(Continued)

*Primary Examiner* — Li Zheng
(74) *Attorney, Agent, or Firm* — Snell & Wilmer L.L.P.

(57) ABSTRACT

The present invention relates to the field of double-stranded RNA (ds RNA) mediated gene silencing of root knot nematodes. The invention particularly provides an effective method for reducing the number of reproducing population and the number of progenies per individual of the root knot nematodes. The present invention also relates to host delivered dsRNA for controlling infection of root knot nematodes.

15 Claims, 9 Drawing Sheets

Figure 1:
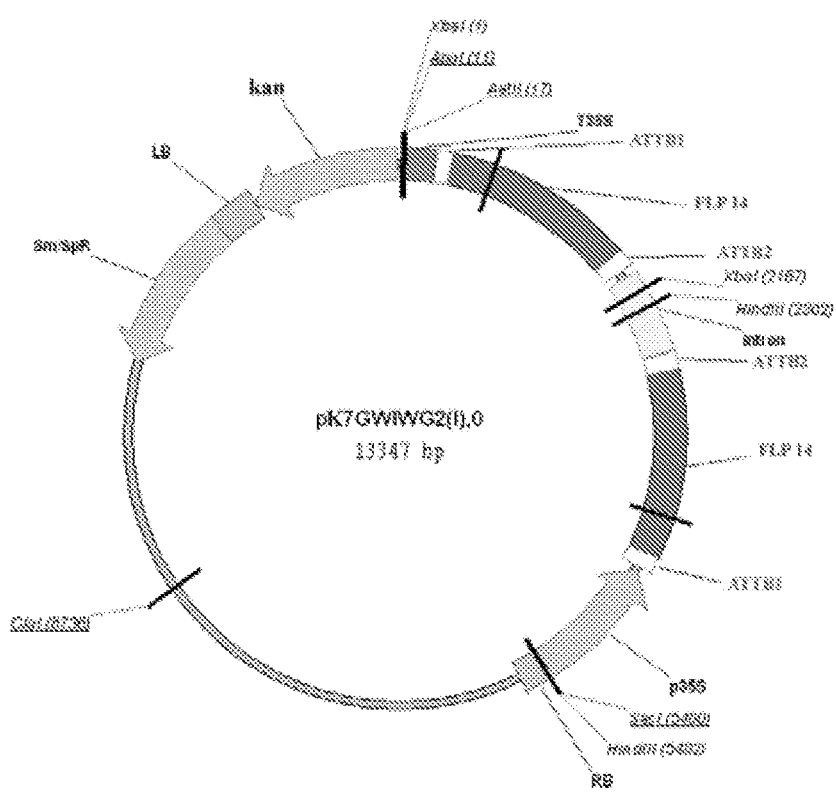

Specification includes a Sequence Listing.

(56) References Cited

OTHER PUBLICATIONS

Maule A.G., "Neuropeptide Signaling Systems—Potential Drug Targets for Parasite and Pest Control," Current Topics in Medicinal Chemistry, 733-758.

McVeigh et al., "The FLP-side of Nematodes," Trends in Parasitology, 22:8, 385-396, (2006).

Mousley et al., "Expression and Bioactivity of Allatostatin-like Neuropeptides in Helminths," International Journal Parasitology, 35: 1557-1567, (2005).

Papolu et al., "Utility of Host Deliverd RNAi of Two FMRF Amide Like Pptides, flp-14 and flp-18, for the Management of Root Knot Nernatode, Meloidogyne Incognita," Plos One, 8:11, (2013).

Roberts, "Current Status of the Availability, Development, and Use of Host Plant Resistence to Nematodes," Journal of Nematology, 24:2, 213-227, (1992).

Xue et al., "The 8D05 Parasitism Gene of Meloddogyne Incognita is Required for Succesful Infection of Host Roots," The American Phytopathological Society, 103:2, 175-181, (2013).

\* cited by examiner

AACGCAAATACTCGTGCTTTCTCTTTTCCCGTCCAGCATCTTTTTCTGCGAG
TCCATGTGTAGCAGCTAATCTTTCAATTCCTTCAGTTACAAAATTTCCTAATTG
AGACAATAAAGTAGAAGATTCATAAAGTTGGCAAAGTAGTAAACGTTCTTCA
TCTCCCCCGGCCAATTGTGCACAATTATCTCCTCCATTTTCAGCTAATCCCGG
TTGTAATAAACAAACCAAAACACAAAATAAAGATAAAATAACCATTAAGAA
GGAATTGTTAGATGGCTGCATA

Figure 2

AACGCAAAUACUCGUGCUUUCUCUUUUCCCGUCCAGCAUCUUUUUCUGCG
AGUCCAUGUGUAGCAGCUAAUCUUUCAAUUCCUUCAGUUACAAAAUUUCC
UAAUUGAGACAAUAAAGUAGAAGAUUCAUAAAGUUGGCAAAGUAGUAAAC
GUUCUUCAUCUCCCCCGGCCAAUUGUGCACAAUUAUCUCCUCCAUUUUCAG
CUAAUCCCGGUUGUAAUAAACAAACCAAAACACAAAAUAAAGAUAAAAUA
ACCAUUAAGAAGGAAUUGUUAGAUGGCUGCAUA

Figure 9 (SEQ ID No.6)

SEQUENCE LISTING

```
<160> NUMBER OF SEQ ID NOS: 6

<210> SEQ ID NO 1
<211> LENGTH: 284
<212> TYPE: DNA
<213> ORGANISM: Artificial Sequence
<220> FEATURE:
<223> OTHER INFORMATION: Artifical sequence

<400> SEQUENCE: 1
aacgcaaata ctcgtgcttt ctcttttccc gtccagcatc tttttctgcg agtccatgtg      60
tagcagctaa tctttcaatt ccttcagtta caaaatttcc taattgagac aataaagtag     120
aagattcata aagttggcaa agtagtaaac gttcttcatc tccccggcc aattgtgcac      180 aattatctcc tccattttca gctaatcccg gttgtaataa acaaaccaaa acacaaaata     240
aagataaaat aaccattaag aaggaattgt tagatggctg cata                      284

<210> SEQ ID NO 2
<211> LENGTH: 22
<212> TYPE: DNA
<213> ORGANISM: Artificial Sequence
<220> FEATURE:
<223> OTHER INFORMATION: flp-14F: Forward Primer for PCR amplification
      fo flp-14 gene

<400> SEQUENCE: 2
aacgcaaata ctcgtgcttt ct                                               22

<210> SEQ ID NO 3
<211> LENGTH: 23
<212> TYPE: DNA
<213> ORGANISM: Artificial Sequence
<220> FEATURE:
<223> OTHER INFORMATION: flp-14R- Reverse Primer for PCR amplification
      of flp-14 gene

<400> SEQUENCE: 3
tatgcagcca tctaacaatt cct                                              23

<210> SEQ ID NO 4
<211> LENGTH: 51
<212> TYPE: DNA
<213> ORGANISM: Artificial Sequence
<220> FEATURE:
<223> OTHER INFORMATION: GV flp-14- Forward primer for cloning flp-14

<400> SEQUENCE: 4
ggggacaagt ttgtacaaaa aagcaggcta acgcaaatac tcgtgctttc t               51

<210> SEQ ID NO 5
<211> LENGTH: 284
<212> TYPE: RNA
<213> ORGANISM: Artificial Sequence
<220> FEATURE:
<223> OTHER INFORMATION: dsRNA sequence

<400> SEQUENCE: 5
aacgcaaaua cucgugcuuu cucuuuuccc guccagcauc uuuuucugcg aguccaugug      60
```

```
uagcagcuaa ucuuucaauu ccuucaguua caaaauuucc uaauugagac aauaaaguag    120
aagauucaua aaguuggcaa aguaguaaac guucuucauc uccccggcc aauugugcac     180 aauuaucucc uccauuuuca gcuaaucccg guuguaauaa acaaaccaaa acacaaaaua    240
aagauaaaau aaccauuaag aaggaauugu uagauggcug caua                    284

<210> SEQ ID NO 6
<211> LENGTH: 51
<212> TYPE: DNA
<213> ORGANISM: Artificial Sequence
<220> FEATURE:
<223> OTHER INFORMATION: GV flp-14- Reverse Primer for cloning flp14
      gene

<400> SEQUENCE: 6
ggggaccact ttgtacaaga aagctgggta tgcagccatc taacaattcc t            51
```

METHOD FOR THE CONTROL OF NEMATODES IN PLANTS

CROSS REFERENCE TO RELATED APPLICATIONS

This application is a U.S. National Phase filing under 35 U.S.C. § 371 of PCT/IB2013/060946, filed on Dec. 14, 2013, which claims priority to Indian Application Number 3876/DEL/2012 filed on Dec. 14, 2012, both of which are incorporated herein by reference in their entirety.

FIELD OF THE INVENTION

The present invention relates to the field of double-stranded RNA (dsRNA) mediated gene silencing of root knot nematodes (RKNs). The invention particularly provides an effective method for reducing the number of reproducing population and the number of progenies per individual of the RKNs. The present invention also relates to host delivered dsRNA for controlling infection of root nematodes.

BACKGROUND AND THE PRIOR ART

Nematodes are a very large group of invertebrate animals generally referred to as roundworms, threadworms, eelworms or nematodes. Some nematodes are plant parasites and can feed on stems, buds, leaves, and in particular on roots. One important genus of plant parasitic nematodes is the root-knot nematode (*Meloidogyne* spp). These parasitic nematodes infect a wide range of important field, vegetable, fruit and ornamental plants.

Various methods based on chemicals, pesticides or fumigants are present for treating or preventing root-knot nematode disease in plants. Chemical agents are often not selective, and exert their effects on non-target organisms, effectively disrupting populations of beneficial microorganisms, for a period of time following application of the agent. Chemical agents may persist in the environment and only be slowly metabolized. The fumigant agent such as chloropicrin is effective in controlling root-knot and other plant-parasitic nematodes. However, this approach is costly and also difficult to apply properly under the prevailing conditions. U.S. Pat. No. 5,013,762 discloses a chemical based method using Bromonitromethane as the active agent for the treatment of nematodes.

The biological control organisms have also been used to try to control nematode disease in crops. Commercially available preparations of biological control organisms are limited in their use to regions that can support the growth of the control organism. Moreover, the outcome of using one organism to control another is unpredictable and subject to a variety of factors such as weather and climate.

Additionally, among plant parasitic nematodes, the RKNs are a leading cause of crop losses. There are several examples of host genes conferring resistance to nematodes in diverse crops. The availability of host plant resistance is substantially limited with appropriate resistance loci lacking for the majority of crops (Roberts, P. A. 1992. Journal of Nematology 24:213-227). In addition, the resistance is limited to only a few RKN species or populations and some resistance genes are heat-sensitive and thus unsuitable for hot production areas. Another limitation of natural resistance genes is the durability of resistance since resistance-breaking populations of RKN can develop after continuous exposure to resistant cultivars, e.g. root-knot resistant tomatoes.

Furthermore, there are six stages and four molts in the development of root knot nematode i.e. egg stage; J1 (i.e. first juvenile stage); M1 (i.e. first molt); J2 (second juvenile stage; sometimes hatch from egg); M2; J3; M3; J4; M4; A (adult). The gene expression may be specific to one or more lifecycle stages only.

FMRFamide (Phe-Met-Arg-Phe) is a neuropeptide from a broad family of FMRFamide-related peptides (FaRPs) all sharing an -RFamide sequence at their C-terminus. FMRFamide like peptides (FLPs) belong to FaRPs comprising the largest family of neuropeptides in nematodes. Most of the structural information of FLPs has been generated from *Caenorhabditis elegans* and the functional data of FLPs comes from the nematode physiological model, *Ascaris suum*. The studies on FLPs in *A. suum* indicate that their vital responsibility for the modulation of nerve and muscle activity in a concentration dependent and reversible manner [Day T. A and Maule A. G (1999), Peptides Vo. 20, pages 999-1019) and Geary T. G et al. (1999), Ann. N Y Acad. Sci. Vol. 897, pages 212-227)]. They are responsible for modulating pharyngeal muscle activity in *A. suum* [Brownlee D. J et al. (1996), Parasitol. Today, vol. 12, pages 343-351]. Similarly, FLPs are also accountable for multiple responses in the ovijector musculature ranging from transient excitation to persistent or transient inhibition [Fellowes R. A et al. (1998) Parasitology 116 (Pt3): 277-2878; Fellowes R. A et al. (2000). Parasitology 121 (Pt 3): 325-336.]. Therefore, these peptides and their associated processes are considered as potential control targets for parasitic helminths [McVeigh P et al. (2006). Trends Parasitol 22: 385-396; Maule A. G. et al. (2002) Curr Top Med Chem 2: 733-758; Mousley A, et al. (2005) Int J Parasitol 35:1557-1567.]. As in the case of *A. suum*, presence of FMRFamide-like immunoreactivity has also been demonstrated in the nervous system of PPNs, *Globodera pallida* and *G. rostochiensis* [Kimber M. J. et al. (2001). Mol Biochem Parasitol 116: 199-208.]. Recently it has been reported that flp-32 in *G. pallida* was responsible for the modulation of locomotory behavior and putatively interacted with at least one novel G-protein coupled receptor [Xue B. et al (2013). Phytopathology 103: 175-181].

FLPs are shown to be present in different parasitic nematodes having similar structural homologues and functions. Consequently, disruption of these activities in PPNs represents an attractive novel control strategy as it would interrupt the worm's ability to hatch, migrate through the soil to reach the host, feed on the host tissue and also to mate. So far, 19 FLPs have been identified in *M. incognita* based on conserved FMRFamide domain analysis of the ESTs and the whole genome sequence by comparative genomics [Abad P et al. (2008). Nat Biotechnol 26: 909-915], out of which six have transcriptional confirmation (flp-1, 7, 12, 14, 16, 18—NCBI GenBank database). MSA (Multiple Sequence alignment) of these six confirmed flp genes showed low nucleotide sequence level conservation among them although they share a common RF-amide sequence at C-terminus. Their uniqueness could therefore be harvested at developing sequence specific knockout module by dsRNA method to avoid off target effects. Further, accurate physiological roles of only few of the FLPs are known and the major information is lacking in *M. incognita* probably due to their small size and obligate relationship with the host which limits the use of standard physiological techniques. Nevertheless, silencing of flp-14 and flp-18 in *M. incognita* has been reported to interrupt the migration of worms in response to the root exudates [Dalzell J J et al. (2010). Int J Parasitol 40: 91-100.; Dalzell J J et al. (2009). Int J Parasitol 39: 1503-1516.].

Charlton et al. (2010) showed that suppression of two *M. incognita* genes (dual oxidase and a subunit of a signal peptidase required for the processing of nematode secreted proteins) using RNAi resulted in the reduction in the number of nematodes by 50%.

U.S. Pat. No. 6,506,559 demonstrates the effectiveness of RNAi against known genes in *C. elegans*. However, it does not reveal any kind of usefulness of RNAi for controlling plant parasitic nematodes.

WIPO patent application WO04/005485 also discloses RNA interference (RNAi) based process for the reduction in nematode reproduction. But, the process does not provide complete effectiveness in reducing nematodes.

US20100068172 relates to methods for controlling nematode infestation via dsRNA mediated gene silencing; whereby nematodes were incubated in the double stranded RNA and whereby the double-stranded RNA is taken up by the nematodes. In one particular embodiment; the methods of the invention are used to alleviate plants from nematode pests. Alternatively; the methods are used for treating and/or preventing nematode infestation on a substrate or a subject in need of such treatment and/or prevention. Suitable nematode target genes and fragments thereof; dsRNA constructs; recombinant constructs and compositions are disclosed.

US20120030834 relates to achieving a plant protective effect through the identification of target coding sequences and the use of recombinant DNA technologies for post-transcriptionally repressing or inhibiting expression of the target coding sequences in the cells of plant-parasitic nematodes. The disclosed gene targets show significant conservation at the nucleotide level between orthologs from different *Meloidogyne* species, facilitating genus-wide targeting by RNA interference.

US20080184391 relates to a transgenic plant having a nucleic acid molecule of a pathogen, wherein the transgenic plant has increased resistance to infection by the pathogen. The nucleic acid molecule of the pathogen is one of (a) a portion of a polynucleotide coding for a protein of the pathogen; (b) a complementary sequence to (a); (c) a combination of (a) and (b); and (d) a combination of (a) and (b) further having a spacer nucleotide sequence. The protein of the pathogen is one of a protein involved in chromatin remodeling in the pathogen, a protein in a recombination pathway of the pathogen, a protein in a nucleotide repair pathway of the pathogen, a protein for post transcriptional processing of RNA in the pathogen, or combinations thereof.

EP1799029 relates to compositions for controlling plant parasites and compositions for increasing root growth, more particularly to nucleic acid compositions for controlling nematode disease or increasing root growth.

US20110150839 relates to a method to obtain transgenic plants resistant to the attack of phytopathogens (i.e. parasites and phytophages) based on RNA interference, Which contemplates the expression of double strand RNA (dsRNA) in the plant tissues, suitable for inhibiting the functionality of a GPCR receptor, Whose functioning is vital for fungi, herbivorous insects or phytopathogenic nematodes.

US20030150017 relates to methods which provide for the genetic control of pathogen infestation in host organisms such as plants, vertebrate animals and fungi. Such methods utilize the host as a delivery system for the delivery of genetic agents, preferably in the form of RNA molecules, to a pathogen, which agents cause directly or indirectly impairment in the ability of the pathogen to maintain itself, grow or otherwise infest a host plant, vertebrate animal or fungus. Also provided are DNA constructs and novel nematode nucleotide sequences for use in same, which facilitate pathogen resistance when expressed in a genetically-modified host. Such constructs direct the expression of RNA molecules substantially homologous and/or complementary to an RNA molecule encoded by a nucleotide sequence within the genome of a pathogen and/or of the cells of a host to effect down regulation of the nucleotide sequence. Particular hosts contemplated are plants, such as pineapple plants, and particular pathogens are nematodes.

CN102352357 relates to a method for inhibiting gene dsRNA of neuropeptide FLPs its application. The invention provides larvae of *M. incognita* in solution of dsRNA reduces root nematodes tendency to migrate host plants, to reduce host plants colonization, and also inhibit nematode reproduction.

Thus, there is a need of an effective method for the inhibition of RKNs, which is capable of achieving the reduction in the multiplication of nematodes at multiple stages and can ultimately help in the reduction of multiple factors/components like the simultaneous decrease in the female population laying eggs, decrease in egg production etc. so as to ensure the complete and successful elimination of the infecting nematodes.

SUMMARY OF THE INVENTION

Accordingly, the main embodiment of the present invention provides a process for controlling the multiplication index of a root knot nematode by reducing the number of reproducing population and number of progeny per individual, said process essentially comprises steps of transforming said host plant cell with a nucleic acid, which express to produce a transcript that forms a double stranded RNA with itself and consequently facilitates the inhibition of the expression of mRNA of said target gene or segment thereof present in said nematode species, wherein said target gene is FMRFamide-like peptide 14 gene and wherein said process causes reduction of about 78% of the multiplication index of said nematode in the transformed host plant cell as compared to the control population of host cell.

Another embodiment of the present invention provides a method of transferring a RNAi vector comprising SEQ ID No.1 in host plants for control of root-knot nematodes, said method comprising steps of:

(a) preparing a vector construct comprising SEQ ID No. 1;
(b) transferring the vector construct of step (a) into an *Agrobacterium* strain;
(c) infecting the host explants with *Agrobacterium* of step (b); and
(d) obtaining the transformed host plants.

Another embodiment of the present invention provide for a RNAi vector construct capable of producing dsRNA transcript.

Another embodiment of the present invention provides for a vector comprising SEQ ID No.1 wherein the vector is a pGEM-T or pK7GWIWG2(I) vector.

Another embodiment of the present invention provide for a use of dsRNA transcript for controlling infection of root-knot nematodes by RNAi or gene silencing of flp-14 gene of root-knot nematodes.

Another embodiment of the present invention provides for a method of expressing dsRNA transcript for RNAi or gene-silencing of flp-14 gene for controlling root-knot nematodes infection, said method comprising steps of:

(a) preparing a vector expression comprising SEQ ID No.1;

(b) transferring the vector of step (a) in a bacteria or a host plant;

(c) obtaining the expression of in vitro and in vivo transcript of dsRNA

Another embodiment of the present invention provides for a method of producing transgenic plants, said method comprising steps of:

(a) preparing a vector construct comprising SEQ ID No. 1;

(b) transferring the vector construct of step (a) into an *Agrobacterium* strain;

(c) infecting the host explants with *Agrobacterium* of step (b); and (d) obtaining the transgenic plants;

Another embodiment of the present invention provides for a use of SEQ ID No. 1 for host delivered expression of dsRNA transcript for controlling infection of root-knot nematodes by RNAi or gene silencing of flp-14 gene of root-knot nematodes.

Another embodiment of the present invention provides for a use of SEQ ID No.1 to express dsRNA transcripts in transgenic plants for controlling infection of root-knot nematodes by RNAi or gene silencing of flp-14 gene of root-knot nematodes.

BRIEF DESCRIPTION OF THE ACCOMPANYING DRAWINGS

The above and other aspects, features, and advantages of certain exemplary embodiments of the present invention will be more apparent from the following description taken in conjunction with the accompanying drawings in which:

FIG. 1: shows flp-14 gene in gate way vector.

FIG. 2: shows flp-14 cDNA sequence (SEQ ID No.1).

Figure 3:
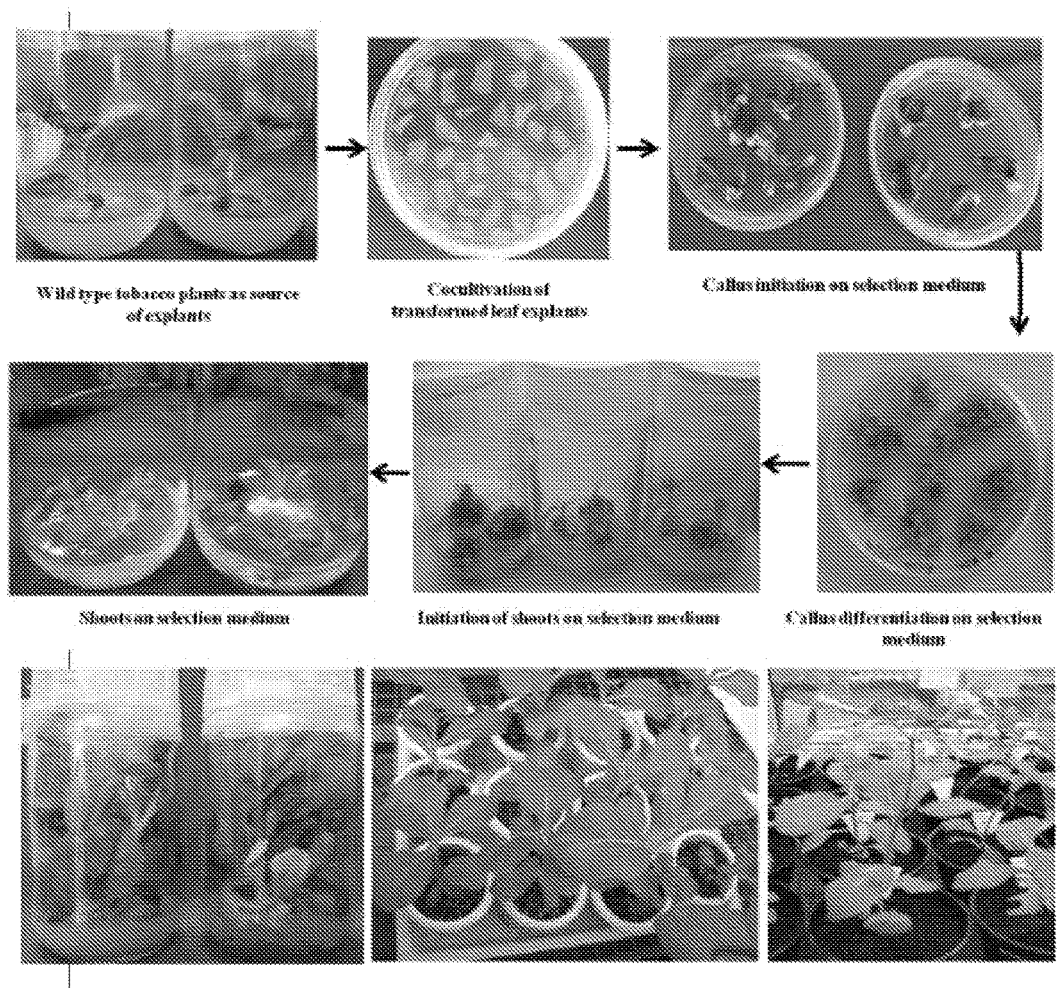

FIG. 3: optimized protocol for *Agrobacterium* mediated transformation of tobacco variety Hawana Petite with flp-14 hairpin RNAi gene construct.

Figure 4:
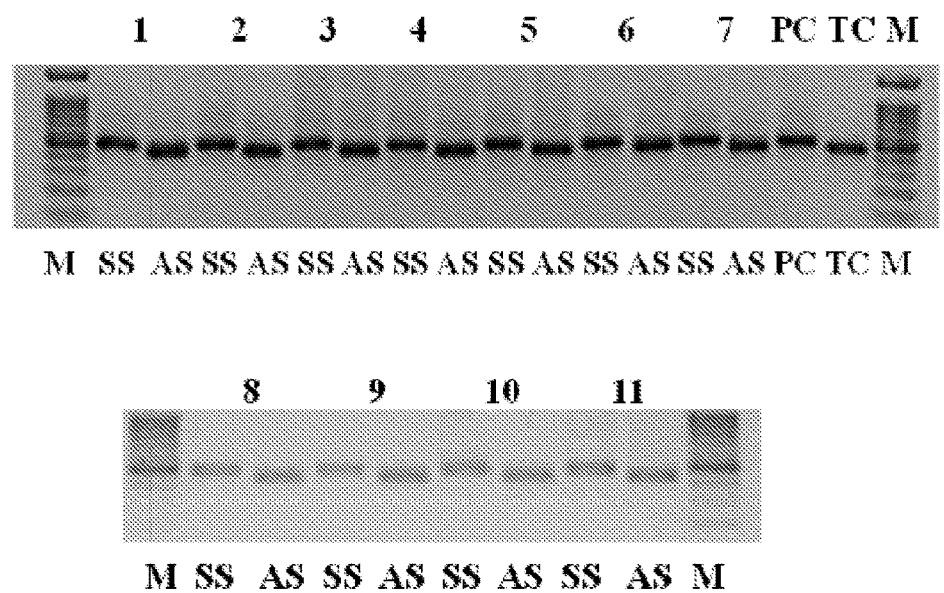

FIG. 4: shows molecular characterization of different primary transgenic events of tobacco expressing flp-14 of *Meloidogyne incognita*.

Figure 5:
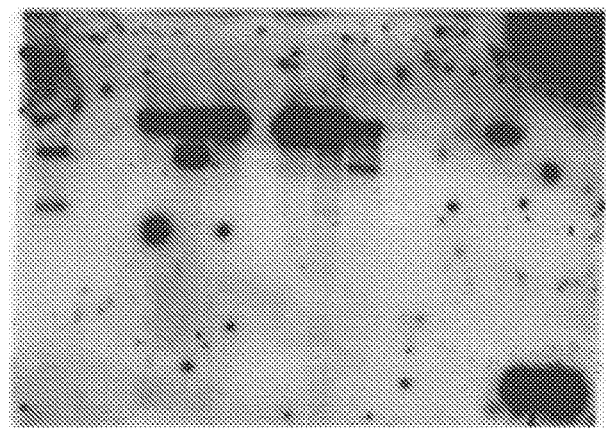
Figure 6:
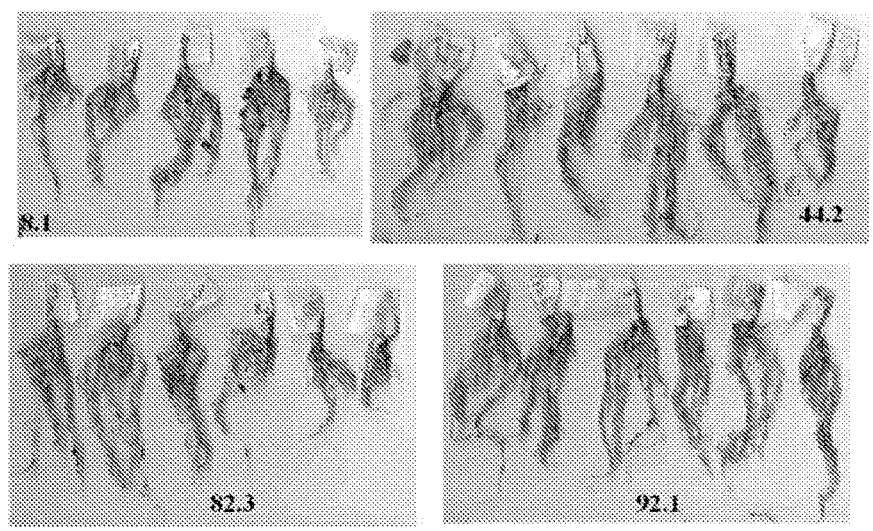

FIG. 5: shows confirmation of integration of flp-14 gene of *M. incognita* in 12 primary transgenic events of tobacco by southern hybridization using gene specific probe.

FIG. 6: shows nematode infected roots of T1 transgenic Tobacco plants expressing flp-14 at 35 days after nematode inoculation.

FIG. 7: Effect of host delivered RNAi of flp-14 on infection and development of *Meloidogyne incognita*

FIG. 8: Percent reduction in the relative transcript levels due to target gene silencing in the females of *M. incognita.*

FIG. 9: shows the dsRNA sequence used in the experiment (SEQ ID No.6).

DETAILED DESCRIPTION OF THE INVENTION

While the invention is susceptible to various modifications and/or alternative processes and/or compositions, specific embodiment thereof has been shown by way of example in the drawings, figures and tables and will be described in detail below. It should be understood, however that it is not intended to limit the invention to the particular processes and/or compositions disclosed, but on the contrary, the invention is to cover all modifications, equivalents, and alternative falling within the spirit and the scope of the invention as defined by the appended claims.

The drawings, figures, tables and protocols have been represented where appropriate by conventional representations, showing only those specific details that are pertinent to understanding the embodiments of the present invention so as not to obscure the disclosure with details that will be readily apparent to those of ordinary skill in the art having benefit of the description herein.

The following description is of exemplary embodiments only and is not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention.

The terms “comprises”, “comprising”, or any other variations thereof, are intended to cover a non-exclusive inclusion, such that one or more processes or composition/s or systems or methods proceeded by “comprises . . . a” does not, without more constraints, preclude the existence of other processes, sub-processes, composition, sub-compositions, minor or major compositions or other elements or other structures or additional processes or compositions or additional elements or additional features or additional characteristics or additional attributes.

Definitions

For the purposes of this invention, the following terms will have the meaning as specified therein:

The terms “double stranded RNA fragment” or “double-stranded RNA region” when used in the context of the present invention refers to a small entity of the double-stranded RNA corresponding with (part of) the target gene. As used herein, the expression “corresponding to” means “complementary to”.

The term “target gene” when used in the context of the present invention refers to a gene that needs to be silenced in the target species. Particular suitable target genes are genes that are involved in an essential biological pathway of the target species, meaning that the target gene is an essential gene to the target species and that gene silencing of the target gene has an adverse effect on the viability or the growth and/or development of the target species. Suitable target genes include genes associated with infection, propagation or pathogenesis of the pest species in the host.

The term “small interfering RNA” or “siRNA” when used in the context of the present invention refers to a class of double-stranded RNA molecules, 20-25 base pairs in length. siRNA plays many roles, but it is most notable in the RNA interference (RNAi) pathway, where it interferes with the expression of specific genes with complementary nucleotide sequence.

The term “FMRFamide-like peptide” or “flp peptide”, when used in the context of the present invention refers to a neuropeptide from a broad family of FMRFamide-related peptides (FaRPs) all sharing an -RFamide sequence at their C-terminus. FMRFamide like peptides (FLPs) belong to FaRPs comprising the largest family of neuropeptides in nematodes.

The term “multiplication index of nematode” when used in the context of the present invention refers to virulence factor of a nematode to reproduce and form progeny in suitable environmental conditions.

The term “complementary DNA” or “cDNA” when used in the context of the present invention refers to single-stranded DNA synthesized from a mature mRNA template.

The term "Critical Difference value", when used in the context of the present invention refers to in statistics, a critical value is the value corresponding to a given significance level. This cutoff value determines the boundary between those samples resulting in a test statistic that leads to rejecting the null hypothesis and those that lead to a decision not to reject the null hypothesis. If the calculated value from the statistical test is less than the critical value, then you fail to reject the null hypothesis. If the calculated statistic is outside of the critical value, then you reject the null hypothesis and are forced to accept the alternate hypothesis.

The present invention provides a method for controlling pest infestation by administering to a pest a target corresponding coding sequence that post-transcriptionally represses or inhibits a requisite biological function in the pest. The present invention particularly utilizes the sequence-specific inhibition of coding sequences using double-stranded RNA (dsRNA), including small interfering RNA (siRNA), as a means for pest control. Further the present invention also relates to unequivocal utility of host delivered RNAi of the FLP gene.

Accordingly, the invention causes knocking down of flp-14 gene for the reduction of nematode population at the interface between host plant i.e. Solanaceous crop like tobacco etc. and the parasite. There is an observed overall reduction of about 78% of the multiplication index of the nematode as compared to the wild type control plants by this method.

The choice of silencing flp-14 gene provides surprising results in terms of higher inhibition capacity because the knock down of flp-14 gene provides options to disrupt different aspects of the parasitic activities just by silencing a single gene. The effects of in vitro or the host delivered dsRNA (double stranded RNA) silencing of flp-14 causes disruption in following factors:

Nematode infection in terms of number of galls produced per plant;

Number of females per plant indicating nematode development;

Number of egg masses reflecting nematode reproduction ability;

Number of eggs per egg mass showing the extend of reproductive suppressiveness;

Multiplication factor which is the ratio of final population to the initial population that determines the population pressure in the soil on the subsequent crop;

The method has been surprisingly successful in the reduction of *M. incognita* population by inhibiting the growth/production of nematodes at various steps of the life cycle, which is illustrated by the following data:

a) Decrease of about 78% of the multiplication index of nematode in the transformed host plant roots as compared to the wild type plant.

b) Decrease of about 41% of the female population laying eggs of nematode as compared to the wild type control plants.

c) Decrease of about 48% in the eggs per egg mass of nematode as compared to the wild type control plants d) Decrease of about 57% in the eggs of nematode as compared to the wild type control plants.

e) The critical difference value for the reduction in multiplication index of the nematode is about 1.91.

f) The critical difference value for the reduction in number of egg per egg mass of the nematode is about 1.27.

g) The critical difference value for the reduction in number of egg per plant of the nematode is about 1.65.

h) The critical difference value for the reduction in number of female nematode population is about 1.83.

i) The critical difference value for the reduction in number of galls is about 1.26.

All the above mentioned parameters have been statistically significantly reduced as compared to the wild type control plants by the present invention.

Also, there is provided a double stranded RNA molecule (dsRNA) for inhibiting the multiplication index of a nematode of *Meloidogyne* species by reducing the number of reproducing nematode and the number of progeny per individual in a host plant cell.

The flp-14 gene has the accession no. AY907829. The total length of the gene is 503 bp while the sequence targeted for post transcriptional gene silencing ranges from 61 bp to 343 bp which consequently results in a 284 bp nucleotide segment. Figure-1 shows flp-14 gene in gate way vector while FIG. 2 shows flp-14 cDNA sequence (SEQ ID No.1).

Here in below, the term complementary DNA (cDNA) refers to single-stranded DNA synthesized from a mature mRNA template.

Thus the present invention further provides for expression of SEQ ID No.1, wherein the expression of SEQ ID No.1 results in production of dsRNA transcript. This dsRNA transcript has been shown to cause RNAi and/or gene silencing of flp-14 gene of root-knot nematodes. The most unique and unexpected finding of the present invention is that the SEQ ID No.1 has been transferred and expressed in the host plant wherein such host plants have been shown develop resistant and/or protection towards the root-knot nematodes. Even more unique and unexpected finding has been that the expression of SEQ ID No.1 results in production or expression of dsRNA transcripts. This expression of dsRNA has been shown have both in vitro and in vivo expression. This expression of dsRNA transcripts causes inhibition the expression of m-RNA of the target gene i.e. flp-14 gene of root-knot nematodes. Thus the present invention shows as unique method of host driven RNAi or gene silencing of flp-14 gene of root-knot nematodes.

The advantage of such host driven RNAi or gene silencing of flp-14 gene of root-knot nematodes is that this method unexpectedly shows disruption of complete life cycle of the root-knot nematodes. Interestingly such disruption is observed in various stages of root-knot nematode i.e. one can see the disruption in no. of infective galls, no. of females, no. of egg masses, etc.

Accordingly, the main embodiment of the present invention provides a process for controlling the multiplication index of a root knot nematode by reducing the number of reproducing population and number of progeny per individual, said process essentially comprises steps of transforming said host plant cell with a nucleic acid, which express to produce a transcript that forms a double stranded RNA with itself and consequently facilitates the inhibition of the expression of mRNA of said target gene or segment thereof present in said nematode species, wherein said target gene is FMRFamide-like peptides 14 gene and wherein said process causes reduction of about 78% of the multiplication index of said nematode in the transformed host plant cell as compared to the control population of host cell.

Another embodiment of the present invention provides a process, wherein said root-knot nematode is of the genus *Meloidogyne.*

Another embodiment of the present invention provides a process, wherein said nematode is *Meloidogyne incognita.*

Another embodiment of the present invention provides a process, wherein said host plant is a monocot or dicot.

Another embodiment of the present invention provides a process, wherein said plant is from Solanaceous family.

Another embodiment of the present invention provides a process, wherein said plant is *Nicotiana tabaccum* or *Solanum melongena*.

Another embodiment of the present invention provides a process, wherein said nucleic acid is transformed through in planta transformation method or soaking method.

Another embodiment of the present invention provides a process, wherein said process reduces about 41% of the female population laying eggs as compared to the control population.

Another embodiment of the present invention provides a process, wherein said process reduces about 48% in the eggs per egg mass as compared to the control population.

Another embodiment of the present invention provides a process, wherein said process reduces about 57% in the eggs as compared to the control population.

Another embodiment of the present invention provides a process, wherein Critical Difference value for the reduction in multiplication index of said nematode is about 1.91.

Another embodiment of the present invention provides a process, wherein Critical Difference value for the reduction in number of egg per egg mass of said nematode is about 1.27.

Another embodiment of the present invention provides a process, wherein Critical Difference value for the reduction in number of egg mass per plant of said nematode is about 1.65.

Another embodiment of the present invention provides a process, wherein Critical Difference value for the reduction in number of female population is about 1.83.

Another embodiment of the present invention provides a process, wherein Critical Difference value for the reduction in number of galls is about 1.26.

Yet another embodiment of the present invention provides a dsRNA having a SEQ ID No 1.

Yet another embodiment of the present invention provides a dsRNA SEQ ID No. 1, for host plant delivered RNAi of flp-14 gene.

Yet another embodiment of the present invention provides a dsRNA SEQ ID No. 1 for in vitro silencing of flp-14 gene.

Another embodiment of the present invention provides a method of transferring a RNAi vector comprising SEQ ID No.1 in host plants for control of root-knot nematodes, said method comprising steps of:
  (e) preparing a vector construct comprising SEQ ID No. 1;
  (f) transferring the vector construct of step (a) into an *Agrobacterium* strain;
  (g) infecting the host explants with *Agrobacterium* of step (b); and
  (h) obtaining the transformed host plants.

Another embodiment of the present invention provides a method of transferring a RNAi vector comprising SEQ ID No.1, wherein the RNAi vector expresses or produces a dsRNA transcript for gene silencing of flp-14 gene of root knot nematodes.

Another embodiment of the present invention provides for a method of transferring a RNAi vector comprising SEQ ID No.1, wherein the expression of SEQ ID No.1 produces a dsRNA transcript for gene silencing of flp-14 gene of root knot nematodes.

Another embodiment of the present invention provides for a method of transferring a RNAi vector comprising SEQ ID No.1, wherein the expression of SEQ ID No.1 produces a dsRNA transcript, wherein the transformed dsRNA sequence confers 22% of the multiplication index of the root knot nematode in the transformed host plant cell as compared to the control population of host cell.

Another embodiment of the present invention provides a method of transferring a RNAi vector comprising SEQ ID No.1 in host plants for control of root-knot nematodes, wherein said root-knot nematode is of the genus *Meloidogyne*.

Another embodiment of the present invention provides a method of transferring a RNAi vector comprising SEQ ID No.1 in host plants for control of root-knot nematodes, wherein said nematode is *Meloidogyne incognita*.

Another embodiment of the present invention provides a method of transferring a RNAi vector comprising SEQ ID No.1 in host plants for control of root-knot nematodes, wherein said host plant is a monocot or dicot.

Another embodiment of the present invention provides a method of transferring a RNAi vector comprising SEQ ID No.1 in host plants for control of root-knot nematodes, wherein said plant is from Solanaceous family.

Another embodiment of the present invention provides a method of transferring a RNAi vector comprising SEQ ID No.1 in host plants for control of root-knot nematodes, wherein said plant is *Nicotiana tabaccum* or *Solanum melongena*.

Another embodiment of the present invention provides a method of transferring a RNAi vector comprising SEQ ID No.1 in host plants for control of root-knot nematodes, wherein said method reduces about 41% of the female population laying eggs as compared to the control population.

Another embodiment of the present invention provides a method of transferring a RNAi vector comprising SEQ ID No.1 in host plants for control of root-knot nematodes, wherein said method reduces about 48% in the eggs per egg mass as compared to the control population.

Another embodiment of the present invention provides a method of transferring a RNAi vector comprising SEQ ID No.1 in host plants for control of root-knot nematodes, wherein said method reduces about 57% in the eggs as compared to the control population.

Another embodiment of the present invention provides a method of transferring a RNAi vector comprising SEQ ID No.1 in host plants for control of root-knot nematodes, wherein Critical Difference value for the reduction in multiplication index of said nematode is about 1.91.

Another embodiment of the present invention provides a method of transferring a RNAi vector comprising SEQ ID No.1 in host plants for control of root-knot nematodes, wherein Critical Difference value for the reduction in number of egg per egg mass of said nematode is about 1.27.

Another embodiment of the present invention provides a method of transferring a RNAi vector comprising SEQ ID No.1 in host plants for control of root-knot nematodes, wherein Critical Difference value for the reduction in number of egg mass per plant of said nematode is about 1.65.

Another embodiment of the present invention provides a method of transferring a RNAi vector comprising SEQ ID No.1 in host plants for control of root-knot nematodes, wherein Critical Difference value for the reduction in number of female population is about 1.83.

Another embodiment of the present invention provides a method of transferring a RNAi vector comprising SEQ ID No.1 in host plants for control of root-knot nematodes, wherein Critical Difference value for the reduction in number of galls is about 1.26. Another embodiment of the present invention provide for a RNAi vector construct capable of producing dsRNA transcript.

Another embodiment of the present invention provides for a vector comprising SEQ ID No.1 wherein the vector is a pGEM-T or pK7GWIWG2(I) vector.

Another embodiment of the present invention provide for a use of dsRNA transcript for controlling infection of root-knot nematodes by RNAi or gene silencing of flp-14 gene of root-knot nematodes.

Another embodiment of the present invention provides for a method of expressing dsRNA transcript for RNAi or gene-silencing of flp-14 gene for controlling root-knot nematodes infection, said method comprising steps of:
  (d) preparing a vector expression comprising SEQ ID No.1;
  (e) transferring the vector of step (a) in a bacteria or a host plant;
  (f) obtaining the expression of in vitro and in vivo transcript of dsRNA Yet another embodiment of the present invention provides for method for expressing dsRNA transcript for RNAi or gene-silencing of flp-14 gene for controlling root-knot nematodes infection, wherein the SEQ ID No.1 expresses dsRNA transcript.

Yet another embodiment of the present invention provides for method for expressing dsRNA transcript for RNAi or gene-silencing of flp-14 gene for controlling root-knot nematodes infection, wherein expression of dsRNA transcript results in RNAi or gene-silencing of flp-14 gene for control of root-knot nematodes.

Yet another embodiment of the present invention provides for method for expressing dsRNA transcript for RNAi or gene-silencing of flp-14 gene for controlling root-knot nematodes infection, wherein said root-knot nematode is of the genus *Meloidogyne.*

Yet another embodiment of the present invention provides for method for expressing dsRNA transcript for RNAi or gene-silencing of flp-14 gene for controlling root-knot nematodes infection, wherein said nematode is *Meloidogyne incognita.*

Yet another embodiment of the present invention provides for method for expressing dsRNA transcript for RNAi or gene-silencing of flp-14 gene for controlling root-knot nematodes infection in host plant, wherein said host plant is a monocot or dicot.

Yet another embodiment of the present invention provides for method for expressing dsRNA transcript for RNAi or gene-silencing of flp-14 gene for controlling root-knot nematodes infection in host plant, wherein said host plant is from Solanaceous family.

Yet another embodiment of the present invention provides for method for expressing dsRNA transcript for RNAi or gene-silencing of flp-14 gene for controlling root-knot nematodes infection in host plant, wherein said host plant is *Nicotiana* tabaccum or *Solanum melongena.*

Yet another embodiment of the present invention provides for method for expressing dsRNA transcript for RNAi or gene-silencing of flp-14 gene for controlling root-knot nematodes infection in host plant, wherein said method reduces about 41% of the female population laying eggs as compared to the control population.

Yet another embodiment of the present invention provides for method for expressing dsRNA transcript for RNAi or gene-silencing of flp-14 gene for controlling root-knot nematodes infection in host plant, wherein said process reduces about 48% in the eggs per egg mass as compared to the control population.

Yet another embodiment of the present invention provides for method for expressing dsRNA transcript for RNAi or gene-silencing of flp-14 gene for controlling root-knot nematodes infection in host plant, wherein said process reduces about 57% in the eggs as compared to the control population.

Yet another embodiment of the present invention provides for method for expressing dsRNA transcript for RNAi or gene-silencing of flp-14 gene for controlling root-knot nematodes infection in host plant, wherein Critical Difference value for the reduction in multiplication index of said nematode is about 1.91.

Yet another embodiment of the present invention provides for method for expressing dsRNA transcript for RNAi or gene-silencing of flp-14 gene for controlling root-knot nematodes infection in host plant, wherein Critical Difference value for the reduction in number of egg per egg mass of said nematode is about 1.27.

Yet another embodiment of the present invention provides for method for expressing dsRNA transcript for RNAi or gene-silencing of flp-14 gene for controlling root-knot nematodes infection in host plant, wherein Critical Difference value for the reduction in number of egg mass per plant of said nematode is about 1.65.

Yet another embodiment of the present invention provides for method for expressing dsRNA transcript for RNAi or gene-silencing of flp-14 gene for controlling root-knot nematodes infection in host plant, wherein Critical Difference value for the reduction in number of female population is about 1.83.

Yet another embodiment of the present invention provides for method for expressing dsRNA transcript for RNAi or gene-silencing of flp-14 gene for controlling root-knot nematodes infection in host plant, wherein Critical Difference value for the reduction in number of galls is about 1.26.

Another embodiment of the present invention provides for a use of SEQ ID No. 1 for host delivered expression of dsRNA transcript for controlling infection of root-knot nematodes by RNAi or gene silencing of flp-14 gene of root-knot nematodes.

Another embodiment of the present invention provides for a use of SEQ ID No.1 to express dsRNA transcripts in transgenic plants for controlling infection of root-knot nematodes by RNAi or gene silencing of flp-14 gene of root-knot nematodes.

Another embodiment of the present invention provides for a transgenic plants expressing SEQ ID No.1 which further produces a dsRNA transcript for controlling infection of root-knot nematodes by RNAi or gene silencing of flp-14 gene of root-knot nematodes.

Another embodiment of the present invention provides for a method of producing transgenic plants, said method comprising steps of:
  (e) preparing a vector construct comprising SEQ ID No. 1;
  (f) transferring the vector construct of step (a) into an *Agrobacterium* strain;
  (g) infecting the host explants with *Agrobacterium* of step (b); and
  (h) obtaining the transgenic plants;

Another embodiment of the present invention provides for a method of producing transgenic plants wherein the expression of SEQ ID NO. 1 produces a dsRNA transcript.

Another embodiment of the present invention provides for a method of producing transgenic plants wherein the expression of SEQ ID NO. 1 produces a dsRNA transcript for control of root-know nematodes.

Another embodiment of the present invention provides for a method of producing transgenic plants wherein the expression of SEQ ID NO. 1 produces a dsRNA transcript which causes RNAi or silencing of flp-14 gene of root-knot nematode.

Another embodiment of the present invention provides for a method of producing transgenic plants wherein the expression of SEQ ID NO. 1 produces a dsRNA transcript which causes RNAi or silencing of flp-14 gene of root-knot nematode, wherein said root-knot nematode is of the genus *Meloidogyne*.

Another embodiment of the present invention provides for a method of producing transgenic plants wherein the expression of SEQ ID NO. 1 produces a dsRNA transcript which causes RNAi or silencing of flp-14 gene of root-knot nematode, wherein said nematode is *Meloidogyne incognita*.

Another embodiment of the present invention provides for a method of producing transgenic plants wherein the expression of SEQ ID NO. 1 produces a dsRNA transcript which causes RNAi or silencing of flp-14 gene of root-knot nematode, wherein said plant is a monocot or dicot.

Another embodiment of the present invention provides for a method of producing transgenic plants wherein the expression of SEQ ID NO. 1 produces a dsRNA transcript which causes RNAi or silencing of flp-14 gene of root-knot nematode, wherein said plant is from Solanaceous family.

Another embodiment of the present invention provides for a method of producing transgenic plants wherein the expression of SEQ ID NO. 1 produces a dsRNA transcript which causes RNAi or silencing of flp-14 gene of root-knot nematode, wherein said host plant is *Nicotiana* tabaccum or *Solanum melongena*.

The following non-limiting examples illustrate specific embodiments of the present invention. They are not intended to be limiting the scope of the present invention in any way.

The invention will now be explained with the help of following examples. However, the scope of the invention should not be limited to these examples as the person skilled in the art can easily vary the proportion of the ingredients and combinations.

EXAMPLES

Example 1: Preparation of Total RNA

The test population is isolated from cultivated soils of India. The freshly hatched *M. incognita* juveniles (J2s) were collected in 1.5 ml microcentrifuge tubes. They were washed 3-4 times with Double distilled sterile water by centrifugation at 6000 rpm for 5 minutes. The tubes with worms were frozen at −80° C. till further use. Total RNA was extracted with the Nucleospin RNA extraction kit (Macherey-Nagel, GmbH, Germany). Total RNA was quantified spectrophotometrically at 260 nm using NanoDrop™ 1000 (NanoDrop Technologies), and used as template for cDNA synthesis by SuperScript II RNase H-Reverse Transcriptase, with an Oligo dt (dt18) primer and 10 mM dNTP. RNA quality and quantity was checked using Nano drop and also on 1% agarose gel for confirmation. RNA was stored at −80° C. to prevent any degradation until further use. This RNA was used for cDNA synthesis.

Example 2: Reverse Transcription for cDNA Synthesis

Total RNA isolated from freshly hatched juveniles was used for synthesis of complimentary DNA (cDNA). 200 ng of total RNA was mixed with 10 μm oligodt (dt18) primer in 0.5 ml PCR tubes. The tubes were incubated at 70° C. for 2 min. The contents of the tube were concentrated at the bottom of the tube by a brief spin and tubes were kept at room temperature. Then other cDNA synthesis components were added (2 μl of 5× $1^{st}$ strand buffer, 1 μl of 20 mM DTT, 1 μl of 10 mM dNTPs and 200 units of reverse transcriptase enzyme) into a total reaction volume of 10 μl. The contents were mixed gently and incubated at 40° C. for 1 hr. After incubation 20 μl RNAse free water was added and again incubated at 72° C. for 7 minutes. This cDNA was used for amplification of target genes.

Example 3: Amplification of Target Gene from cDNA Using Polymerase Chain Reaction (PCR) and Agarose Gel Electrophoresis The target gene is PCR amplified from cDNA using the gene specific primers already designed and synthesized. The target gene is preferably flp-14. PCR amplification reactions were performed in 30 μl reaction volumes containing 1.5 μl 10× assay buffer (100 mM Tris-HCl (pH 8.8 at 25° C.), 500 mM KCl, 15 mM $MgCl_2$, 0.1% gelatin, 0.05% Tween 20 and 0.05% NP-40), 200 μM each of dATP, dCTP, dGTP and dTTP (Promega Madison, Wis., USA), 16 ng primer, 1 unit of Taq polymerase (MBI Fermentas, Genetix, India) and 1 μl cDNA. A 284 bp region of flp-14 (GEnBank: AY907829) was thus amplified from the cDNA using primers as given in Table 1.

TABLE 1

Primers used for PCR amplification of flp-14

| Name | Accession | Sequence (5'-3') | Length (bp) | TM (° C.) |
|---|---|---|---|---|
| flp-14 F (SEQ ID No. 2) | AY907829 | AACGCAAATAC TCGTGCTTTCT | 284 | 60 |
| flp-14 R (SEQ ID No. 3) | | TATGCAGCCATC TAACAATTCCT | | |

Amplification was carried out in Eppendorf Gradient Thermal Cycler programmed for 45 cycles. The PCR cycling conditions for the target genes are given in table 2. 5 μl aliquots of amplification products were loaded on 1.5% agarose gels prepared in 1×TAE buffer (pH 8.0), separated by electrophoresis (5 V/cm for 2.5 hr) and stained with ethidium bromide. The gels were visualized using a gel documentation system (Alpha Image Analyzer, USA). Table 2 provides for cycling conditions used for amplification of the target gene.

TABLE 2

Cycling conditions used for amplification of the target gene

| S No | PCR steps | Temperature | Time |
|---|---|---|---|
| 1 | Denaturation | 94° C. | 4 min. |
| | | 94° C. | 1 min. |
| 2 | Annealing Tm | 60° C. | 30 sec. |
| 3 | Extension | 72° C. | 2 min. |
| | | 72° C. | 10 min. |

Example 4: Cloning and Sequencing of Target Genes 4.1 Ligation

Purified PCR product was cloned into pGEM-T easy vector (Promega, USA). Ligation mixture was prepared by adding 4 µl of purified DNA, 4 µl of ligation buffer (supplied with kit), 1 µl (50 ng) of pGEM-T easy vector and 1.0 µl of T4 DNA ligase in a microcentrifuge tube. The reaction mixture was mixed well by a short spin and ligation was carried out overnight at 4° C.

4.2 Transformation of E. coli

10 µl of ligation mixture was added to 200 µl of competent cells present in the microcentrifuge tubes and kept on ice for 30 min. The bacterial cell-DNA mixture was then subjected to heat shock at 42° C. for 90 sec and immediately kept on ice for at least 2 min. About 800 µl of LB was added to the heat-shocked bacterial cells and allowed to grow at 37° C. for 1 hr with continuous shaking at 180 rpm. The tube containing culture was centrifuged for 30 sec at 8000 rpm and re-suspended aseptically in 200 µl of LB media and spread aseptically on Luria agar (LA) plate containing IPTG, X-gal and ampicillin. 100 ml LA contained 100 µl ampicillin (50 mg/ml), 200 µl X-gal (20 mg/ml) and 20 µl IPTG (200 mg/ml). The plates were incubated overnight at 37° C. and on the next day positive transformants containing the inserts were selected on the basis of blue/white colony colour. The white colonies were transferred to a master plate containing ampicillin and incubated at 37° C. for overnight.

4.3 Colony PCR for Confirmation of the Recombinant Bacterial Colonies with Gene Inserts The white colonies were confirmed by colony PCR with a little modification of the protocol as described by Sambrook et al., (2001). The single putative positive white colonies growing on IAX-plate were picked up with the help of toothpicks and dipped in 10 µl PCR reaction mixture with gene specific primers prepared as already mentioned above. Amplification was carried out in Eppendorf gradient thermal cycler using the above mentioned PCR cycling conditions.

4.4 Confirmation of the Target Gene Inserts by Sequencing

The confirmed positive bacterial colonies were grown overnight in LB with ampicillin at 37° C. and the overnight grown fresh cultures were used for plasmid preparation. The plasmid preparation was done using NucleoSpin plasmid prep kit (Macherey-Nagel, GmbH, Germany). Plasmids with inserts were sent for sequencing to commercial sequencing centre. Sequencing of the inserts in the plasmid was done using universal M13 forward and reverse primers. The sequences were then confirmed by BLAST analysis for their identity.

4.5. Plasmid Preparation

Plasmids of the recombinant colonies were prepared using NucleoSpin plasmid prep kit (Macherey-Nagel, GmbH, Germany) as per the manufacturer's protocol.

Example 5: In Vitro Transcription for Double Stranded RNA Synthesis 5.1 Template Preparation for In Vitro Transcription (IVT).

Plasmids of the sequence confirmed clones were used for preparing the DNA template for in vitro transcription.

The target gene insert is then PCR amplified from the respective recombinant plasmids using M-13 forward and reverse primers. PCR was carried out with an initial denaturation at 94° C. for 4 min followed by 35 cycles. Each cycle consisted of 94° C. for 1 min, 55° C. for 30 sec, 72° C. for 1 minute and a final extension of 72° C. for 10 min. 2 µl of PCR product was mixed with loading dye and electrophoresed on 1% agarose gel prepared in 1× Tris-acetate-EDTA (TAE) buffer containing ethidium bromide (0.5 µg/ml). Electrophoresis was carried out at 90V for 30 minutes. The gels were visualized using Alpha Image analyzer (USA).

5.2 PCR purification:

PCR amplified product was purified using Qiagen PCR purification kit (Qiagen, GmbH, Germany) as per the protocol described by manufacturer. The eluted DNA was stored at −20° C. The purified PCR product of the target gene was used for synthesis of dsRNA by in vitro transcription.

5.3 In Vitro Transcription for Synthesis of ssRNA

PCR products of the flp-14 gene has T7 and Sp6 RNA polymerase promoter sites at 5' and 3' ends which can be used for in vitro transcription reaction with MEGAscript RNAi kit $T_7$ and $Sp_6$ from Ambion (Ambion, Austin, Tex., USA). The composition of the reaction mixture is given in the below table 3:

TABLE 3

Composition of reaction mixture for in vitro transcription of the target gene

| Sp6 | | T7 | |
|---|---|---|---|
| Template DNA | 8 µl | Template DNA | 8 µl |
| 10x buffer | 2 µl | 10 × buffer | 2 µl |
| (100) dATP | 2 µl | (100) dATP | 2 µl |
| (100) dATP | 2 µl | (100) dATP | 2 µl |
| (100) dATP | 2 µl | (100) dATP | 2 µl |
| (100) dATP | 2 µl | (100) dATP | 2 µl |
| RNA polymerase enzyme | 2 µl | RNA polymerase enzyme | 2 µl |
| Total volume | 20 µl | Total volume | 20 µl |

Both the Sp6 and T7 mixtures were incubated at 37° C. for 20-23 hours in a thermostat (Eppendorf, Germany). After incubation 30 µl lithium chloride and 30 µl nuclease free water was added and incubated for 3 hrs at −20° C. The tubes were centrifuged at 15,000 rpm for 20 min at 4° C. (5810 R, Eppendrof, Germany) to pellet the single stranded RNA (ssRNA). The supernatant was carefully removed, pellet was washed in 300 µl 70% ethanol and the tubes were centrifuged at 15,000 rpm for 10 minutes at 4° C. Again the supernatant was carefully removed and pellet was dissolved in 20 µl nuclease free water. The quantity and quality of ssRNA was confirmed by running 1 µl of ssRNA on 1% agarose gel.

5.4 Preparation of Double Stranded RNA (dsRNA)

The two ssRNA strands generated as above from each of Sp6 and T7 reactions were mixed together and hybridized by incubation at 65° C. for 5-10 minutes followed by 37° C. for 30 min. The quantity and quality of dsRNA was checked on 1% agarose gel for confirmation and stored in −20° C. This dsRNA was used for all experimental purposes. The dsRNA were synthesized from two ssRNA strands and cloned in pGEM-T vector for further use (FIG. 9; SEQ ID NO.6). This sequence was further used for in vitro expression studies as discussed in below sections of the examples

Example 6: Agrobacterium Mediated Transformation of Tobacco Variety Hawana Petite with flp-14 Hairpin RNAi Gene Construct: Development of RNAi Constructs for flp14 for in Planta Validation The pK7GWIWG2(I) vector (RNAi GATEWAY ready) (Karim et al. 2002. Trends Plant Sci. Vo. 7: 193-195) was obtained from VIB Department of Plant Systems Biology, Ghent University, Belgium). Partial sequence of flp-14 (284 bp) was initially amplified from pGEM-T clone and cloned into the entry vector (pDONR 207). Primer details are given in Table 7. The gene fragments were subsequently cloned into GATEWAY ready pK7GWIWG2(I) RNAi vector in sense and antisense orientation intervening with an intron by GATEWAY recombination based cloning (Invitrogen) (FIG. 2; comprising SEQ ID No. 1). These RNAi constructs were transformed to E. coli (DH5α) cells and colony PCR was performed using three different sets of primers (gene specific forward and reverse; CaMV 35S promoter forward and attB2 reverse; CaMV 35S terminator forward and attB2 reverse; nptII forward and reverse primers) to confirm the orientation of the target gene. The PCR products were sequenced and BLAST analysis was done to ensure that PCR reaction specifically amplified the target gene. Further Agrobacterium tumefaciens strain LBA4404 was transformed with the recombinant construct by electroporation and used for validation studies in Nicotiana tabacum.

FIG. 3 shows an optimized protocol for Agrobacterium mediated transformation of tobacco variety Hawana Petite with flp-14 hairpin RNAi gene construct. FIG. 4 shows the molecular characterization of different primary transgenic events of tobacco expressing flp-14 of M. incognita while FIG. 5 shows confirmation of integration of flp-14 gene of *M. incognita* in 12 primary transgenic events of tobacco by southern hybridization using gene specific probe. While, FIG. 6 shows nematode infected roots of T1 transgenic Tobacco plants expressing flp-14 at 35 days after nematode inoculation.

Example 7: Process for In Vitro RNAi Gene Silencing Through Soaking in dsRNA

The in vitro RNAi was carried out by soaking method according to the method described by Urwin et al., 2002. *M. incognita* egg masses were handpicked from the roots of 8-12 weeks post nematode infected tomato plants. Egg masses were kept on nylon mesh fused in polyethylene ring for supporting in medium size petriplate for hatching at room temperature of 25-30° C. for 24-48 hr. Freshly hatched juveniles were collected in 1.5 ml centrifuge tubes. The collected preparasitic $J_2$s were washed with DD sterile water by centrifugation (6000 rpm for 5 min) to get clean nematodes.

The nematodes were soaked in dsRNA (SEQ ID No.6) solution so that it could be taken up by the nematodes. About 3000-5000 juveniles were soaked in a 100 μl solution containing 50 μl of 50 mM octopamine (DL-octopamine hydrochloride, Sigma, Poole, Dorset, U.K), 3 μl dsRNA (2 μg/μl) and 47 μl nuclease free water. Soaking was done in dsRNA corresponding to flp-14 gene. Similarly another lot of worms were soaked in dsRNA solution corresponding to flp-14 gene without octopamine. Control worms were soaked in 100 μl of sterile spring water. All the soaks were carried out at room temperature in siliconized 1.5 ml microcentrifuge tubes kept at room temperature. The tubes were covered with aluminium foil and incubated on a rotator rotating at 10 rpm for 16-18 hr. After incubation the nematodes were washed 3-4 times with autoclaved spring water by centrifugation at 6000 rpm for 5 min to remove the dsRNA and octopamine. The nematodes were examined under microscope for mobility and normal behaviour and further used for experimental studies. Octopamine is a biologically active amine, which is a neurotransmitter, stimulates the pharyngeal pumping and ingestion (Urwin et al., 2002).

The nematode resistance was measured in terms of nematode multiplication factor. It was measured as percentage reduction in transgenics over the wild type plants. The result of gene inhibition for different genes is provided in Table 4.

The data in table 4 shows the effect of silencing flp-14 gene of *M. incognita* through host delivered dsRNA or RNAi using tobacco. The silencing of flp-14 has affected the entire nematode life cycle along with the disease cycle. This is reflected in statistically significant reduction in infection scored in terms of number of galls produced per plant at both 1% and 5% CD. The number of galls is one of the primary parameters to measure the nematode resistance since only a successfully established nematode could induce the gall formation on the host roots. Each gall can be formed by one or more nematodes. Thus, silencing of flp-14 resulted in reduction of number of females per plant which is an important quantitative measure for determining the extent of nematode development. In view of this, silencing of flp-14 has specifically reduced statistically significant number of females per plant (15.1 to 40.9%). Following the development, successful reproduction is an essential component of parasites survival in nature. Number of egg masses produced per plant is therefore, important. A drastic reduction ranging from 34.5 to 57.2% in the number of egg masses was observed in transgenic plants.

TABLE 4 showing the effect of host delivered RNAi silencing of flp-14 on *M. incognita* infecting transgenic tobacco

| S .No | Treatment | No. of galls | No. of females | % reduction of females over control | No. of egg masses/ plant | % reduction of egg masses over control | % of females reproducing | No. of eggs per egg mass | % reduction in eggs/ egg mass over control |
|---|---|---|---|---|---|---|---|---|---|
| 1 | Wild type | 121 (10.98) | 146.8 (12.09) | — | 130 (11.37) | — | 88.6 | 427.6 (20.68) | — |
| 2 | Flp14 - 8.1 | 102.6 (10.14) | 124.6 (11.14) | 15.1 | 72.4 (8.48) | 44.3 | 58.1 | 241 (15.52) | 43.6 |
| 3 | Flp14 - 44.2 | 72 (8.47) | 121.4 (10.99) | 17.3 | 85.2 (9.23) | 34.5 | 70.2 | 253 (15.90) | 40.7 |
| 4 | Flp14 82.3 | 66.2 (8.15) | 86.8 (9.34) | 40.9 | 55.6 (7.47) | 57.2 | 64.1 | 223.2 (14.93) | 47.8 |
| 5 | Flp14 92.1 | 106.6 (10.34) | 177.2 (13.27) | −20.7 | 85.4 (9.22) | 34.3 | 48.2 | 227.6 (15.08) | 46.8 |
| | F | 15.28** | 10.12** | | 12.04** | | | 57.91** | |

TABLE 4-continued showing the effect of host delivered RNAi silencing of flp-14 on M. incognita infecting transgenic tobacco

| S.No | Treatment | No. of galls | No. of females | % reduction of females over control | No. of egg masses/ plant | % reduction of egg masses over control | % of females reproducing | No. of eggs per egg mass | % reduction in eggs/ egg mass over control |
|---|---|---|---|---|---|---|---|---|---|
| | CD (p = 0.05) | 0.93 | 1.34 | | 1.21 | | | 0.93 | |
| | CD (p = 0.01) | 1.26 | 1.83 | | 1.65 | | | 1.27 | |

This could be due to either feeding disruption leading to reduced development or reproductive disruption or both since silencing flp-14 could have disrupted multiple metabolic activities as it has multifunctional roles as mentioned. In transgenic plants, number of females reproducing was only in the range of 48.2 to 70.2% whereas in wild type it was 88% indicating a great disruption in reproduction.

Further, number of eggs per egg mass is another dimension to measure the reproduction potential. A significant reduction was observed in the eggs per egg mass ranging from 40.7 to 47.8%.

All the aspects of infection, development and reproduction will affect the final multiplication index or factor calculated. Multiplication factor at the end of life cycle of parasite determines potential damage from season to season in agriculture fields. In the present invention, the multiplication factor has been reduced in the range of 61.4 to 77.8% in the four independent transgenic events. Interestingly, in the event flp-14-92.1, even though the number of females per plant was approximately 20% more than the wild type, only 48% of the females have reproduced compared to 88% in wild type. Further in the same event 46.8% reduction was seen in the number of eggs which led to 64.3% reduction in multiplication factor over the wild type control.

Overall, it is demonstrated for the first time that silencing of flp-14 in a susceptible tobacco variety results in drastic reduction in infection, development and reproduction of M. incognita and this exhibits opportunities for potential application in all the Solanaceous crop plants to produce resistant varieties with capacity to serially reduce multiplication of nematodes from season to season. A similar approach can also be extended to other groups of crops wherever this nematode is a serious problem as it is known to infect more than 2000 hosts worldwide.

Example 8: Studies for Determining the Gene Silencing Effect Through the dsRNA Molecule of the Invention 1. Bioassay for In Vitro RNAi Gene Silencing of Flp-14 on Pluronic Gel for Determining the Gene Silencing Effect on Host Finding Behavior of M. incognita:
A. Pluronic Gel Preparation Pluronic F-127 is a block copolymer based on ethylene oxide and propylene oxide. Pluronic gel F-127 is a stable and non-toxic compound that is widely used in medical and pharmaceutical fields. Pluronic gel is solid at room temperature and liquid at temperatures below 15° C. when the gel concentration is about 20-30%. The transparent gel system can be used to record nematode movement in the presence of the host plants and to compare attraction and infectivity among different strains or species of nematodes on one host. This gel system is also applicable for study of the molecular biology of host-nematode interaction before and after the early stage of infection in vivo (Wang, 2009). To make 100 ml gel, 23 g Pluronic F-127 powder (NF Prill Poloxamer 407, BASF, Mt Olive, N.J., USA) was added to 80 ml cold, sterile water and allowed to dissolve with continuous stirring for 24 h at 4° C. The dissolved gel was stored at 4° C. until further use. A 23% solution is a semisolid gel at room temperature but is liquid at temperature of 15.0 and below. Nematodes can move freely through the highly transparent gel, thus making the assay three-dimensional. Here we test the utility of pluronic gel for examining effect of gene silencing on attraction of M. incognita juveniles to live tomato roots kept on pluronic gel and other aspects of their behaviour.

B. Germination of Tomato Seeds

Tomato ((Lycopersicon esculentum var Pusa Ruby) seeds were surface sterilized with alcohol for 3-4 minutes followed by washing 3-4 times with DD autoclaved water. Seeds were germinated on moist filter paper kept in petriplates.

2. Effect of In Vitro Gene Silencing by Soaking in dsRNA of Flp-14 on Attraction and Penetration of M. incognita Using Pluronic Gel 3-4 days old germinated tomato seedlings of uniform size were selected and washed with DD water for attraction and penetration studies. Experiment on effect of gene silencing on nematode attraction and penetration to tomato roots was set up in 6 cm diameter petriplates placed on ice in a tray to keep the pluronic gel in liquid state while the experiment was set up.

The juveniles soaked in dsRNA with octopamine and without octopamine dsRNA were washed 3-4 times separately using sterile spring water to remove dsRNA and octopamine. The number of J2 in the suspension was determined by counting the worms in five 10 µl aliquot separately, the mean calculated and multiplied by the total volume for determining the total number of nematodes present in the suspension. For each plate 1000 nematodes were added followed by topping with 5 ml of 23% pluronic gel. Two tomato seedlings were placed opposite to each other in petriplate and then petriplates were taken out from the ice trays. The petriplates were kept at room temperature for the gel to set. Eight replications were used for each treatment. Worms were soaked in dsRNA of flp-14 gene in presence of a neurotransmitter, octopamine which helps in dsRNA uptake. Worms soaked in spring water and octopamine served as controls.

2.1. Observations Recorded

To determine the effect of gene silencing on nematode attraction and penetration to tomato root tips in terms of number of nematodes in the root tips at two time intervals viz., 24 hr and 72 hr. The number of nematodes penetrated was determined by staining the roots with acid fuchsin (Byrd et al., 1968) at 24 and 72 hr after inoculation. Table 5 exhibits the effect of silencing flp-14 on nematode attraction and infection ability or penetration into the host plant.

2.2. Byrd's Staining and Bleaching Method

The tomato plant roots were gently taken out of the pluronic gel and washed in water for 1-2 minutes to remove adhering pluronic gel. For observing juveniles penetrated into roots, tomato roots tips were collected separately and soaked in 4% sodium hypochlorite (NaOCl) in small beakers for 4 min and then washed with water thrice to remove bleaching agent. The washed root tips were then plunged into another small beaker containing boiling mixture of 100 ml of water and 4 ml of acid fuchsin stain from stock solution (3 g of acid fuchsin+250 ml of acetic acid+750 ml distilled water) which was heated to boil for 30 seconds. These stained roots were washed in water to remove excess stain and transferred to a petri plates containing glycerol and left for 12 hr to de stain (Byrd et al., 1983). The stained nematodes in roots were observed and counted under stereoscopic binocular microscope (V20, Carl Zeiss, Germany).

TABLE 5

Effect of gene silencing on nematode penetration in to host roots in the presence of octopomine

| S. No | Treatment | Nematodes inside root at 24 hr | % reduction over control | Nematodes inside root at 72 hr | % reduction over control |
| --- | --- | --- | --- | --- | --- |
| 1 | Water control | 103.25$^b$ | — | 75$^b$ | — |
| 2 | Otopamine control | 123$^b$ | +19.1 | 78$^b$ | +4 |
| 3 | Flp-14 | 53.25$^a$ | 48.4 | 46.75$^a$ | 37.7 |
|   | Mean | 93.16 |  | 66.58 |  |
|   | F | 26.03 |  | 24.03 |  |
|   | p | <0.001 |  | <0.001 |  | be degraded since in vitro RNAi can only provide temporary or transient silencing effect. So the in vitro RNAi silencing indicates that if there is continuous silencing of flp-14, it could be more effective. Host delivered dsRNA can provide such continuous silencing effect as dsRNA of the target gene can be taken up by the feeding nematode along with the nutrients. In view of this, transgenic tobacco expressing dsRNA of flp-14 was generated for host delivered flp-14 dsRNA.

3. Effect of In Vitro Gene Silencing by Soaking in dsRNA of Flp-14 on Attraction and Penetration of M. incognita on Adzuki Beans Seeds (2$^{nd}$ Bioassay)

Seeds of Adzuki beans (Vigna angularis) belonging to family Fabeaceae were washed with a detergent, lablolin. Detergent was removed by washing the seeds 3-4 times with double distilled sterile water (DD water). The washed seeds were surface sterilized with 4% sodium hypochloride for 8 min. Again the seeds were washed 3-4 times with double distilled sterile water and placed on moist filter paper for germination in petriplates.

3.1. Raising and Inoculation of Adzuki Bean Seedlings in CYG Growth Pouch 3-4 days germinated seeds were first washed with DD sterile water and seed coat was removed. Seeds were then transferred in to CYG growth pouches for further growth. Pouches were supported by thermocoal sheets kept in rectangular black plastic boxes placed in plant growth chamber. Plants were watered regularly and monitored for healthy growth.

3.2. Observations Recorded 30 days after inoculation, plants were harvested and observation were recorded on number of galls per plant, number of females pre gall, total number of females per plant, number of egg masses per plant and number of eggs per eggmass in the following table 6.

TABLE 6

Effect of silencing flp-14 on nematode development and reproduction in Adzuki beans plants

| S.No | Treatment | No. of galls | % decrease over control | No. Of females | % decrease over control | No. of egg mass | % decrease over control | No. of eggs per egg mass | % decrease over control |
| --- | --- | --- | --- | --- | --- | --- | --- | --- | --- |
| 1 | Water control | 41.3 (6.4) | 0 | 73.2 (8.54) | 0 | 73.2 (8.54) | 0.00 | 667.2$^b$ (25.81) | 0 |
| 2 | Octopamine | 31 (5.54) | 24.94 | 50.6 (7.1) | 30.87 | 50.5 (7.09) | 31.01 | 733.9$^c$ (27) | −10.00 |
| 3 | flp-14 | 30.1 (5.48) | 27.12 | 35.6 (5.95) | 51.37 | 22.5 (4.72) | 69.26 | 431.9$^b$ (20.6) | 35.27 |
|   | F | 10.593 |  | 22.222 |  | 21.217 |  | 69.87 |  |
|   | P | <0.001 |  | <0.001 |  | <0.001 |  | <0.001 |  |

Data in Table 5 shows that silencing of flp-14 greatly reduced the attraction and penetration of M. incognita juveniles into the tomato roots at both 24 and 72 hrs. There was a reduction of about 48.4% and 46.74% at 24 hr and 72 hr respectively. Octopamine did not have any negative effect on the attraction and penetration. The reduction in penetration was statistically significant at both the intervals tested. The reduction at 72 hrs was almost the same as at 24 hrs indicating that there was no revival in the nematode activity even after 72 hrs by which time the silencing effect should Data in above Table 6 regarding the effect of in vitro silencing of flp-14 on infection, development and reproduction indicates that there was about 27.12% decrease in number of galls. However about 51.37% decrease in number of females was observed indicating the effect of silencing flp-14 on nematode development. Further number of egg masses and eggs per egg mass was reduced by 69.26% and 35.27% respectively. This strongly suggested that the silencing of flp-14 interfered with both development and reproduction even though the silencing was only transient as it was in vitro RNAi. In view of this the data strongly supported flp-14 as a potential target for interfering with various parasitic activities of M. incognita and hence the gene flp-14 was further used for plant expression.

Example 9: Molecular Validation of Effective Gene Silencing of Flp-14 Gene Using qPCR Juveniles soaked overnight in dsRNA of flp-14 as mentioned above were washed and frozen immediately in liquid nitrogen. Control worms were soaked in sterile water. Total RNA was extracted with the Nucloespin RNA extraction kit (Macherey-Nagel, GmbH, Germany). Total RNA was quantified spectrophotometrically at 260 nm using NanoDrop™ 1000 (NanoDrop Technologies), and used as template for cDNA synthesis by SuperScript II RNase H-Reverse Transcriptase, with an Oligo dt (dt18) primer and 10 mM dNTP. The resultant cDNAs were used in triplicate qPCRs to analyse the transcript levels post soak for all the treatments. Table 7 shows primer sequence information and qPCR was conducted using Mesa blue SYBR Green qPCR SuperMix kit (Eurogentec). Primer sets to be used for qPCR were optimized for working concentration, annealing temperature and analyzed by disassociation curve for contamination or non specific amplification by primer-dimer as standard.

TABLE 7 primers for Flp-14 gateway Vector

| Primer name | Primer sequence |
|---|---|
| Forward primer (GVflp-14 F) (SEQ ID No. 4) | GGGGACAAGTTTGTACAAAAAAGCAGGCTAACGC AAATACTCGTGCTTTCT |
| Reverse primer (GV flp-14 R) (SEQ ID No. 5) | GGGGACCACTTTGTACAAGAAAGCTGGGTATGCA GCCATCTAACAATTCCT |

Further, the transformed flp-14 gene is well expressed in different $T_1$ transgenic events, which is demonstrated by the below Table 8:

TABLE 8

Comparative expression of flp-14 by qPCR in different $T_1$ transgenic events of tobacco

| S. NO | Event Number | Ct Mean | Fold Change |
|---|---|---|---|
| 1 | 44.2-3 | 21.57 | 448 |
| 2 | 44.2-8 | 21.11 | 506 |
| 3 | 44.2-9 | 21.9 | 322 |
| 4 | 8.1-2 | 18.05 | 3821 |
| 5 | 8.1-8 | 29.67 | 1.36 |
| 6 | 82.3-2 | 20.77 | 626 |
| 7 | 82.3-3 | 23.63 | 93 |
| 8 | 82.3-4 | 22.92 | 147 |
| 9 | 82.3-8 | 23.62 | 84.5 |
| 10 | 92.1-3 | 21.84 | 310 |
| 11 | 92.1-7 | 21.93 | 319 |
| 12 | 92.1-8 | 21.7 | 382 |

Data in above Table 8 regarding the expression analysis of flp-14 in various transgenic events of tobacco reveals that the expression of flp-14 was good in most of the events as indicated by the fold change. The expression fold change is determined by comparing with the wild type control plants.

The present invention will be explained further with reference to non-limiting embodiments of the invention.

In an embodiment of the present invention, there is provided a concatemer dsRNA design, which allows combining of several short fragments in one longer dsRNA construct and allowing to increase the efficacy of the control of the pests' viability, growth and/or development.

In another embodiment of the present invention, there is provided a plant transformation vector containing sequences from more than one gene, thus allowing production of more than one dsRNA for inhibiting expression of two or more genes in cells of a target nematode. One skilled in the art will readily appreciate that segments of DNA whose sequence corresponds to that present in different genes can be combined into a single composite DNA segment for expression in a transgenic plant. Alternatively, a plasmid of the present invention already containing at least one DNA segment can be modified by the sequential insertion of additional DNA segments between the enhancer and promoter and terminator sequences.

In another embodiment of the present invention, the genes of M. incognita to be inhibited can be obtained from the same plant-parasitic nematode species in order to enhance the effectiveness of the control agent. In certain embodiments, the genes can be derived from different plant-parasitic nematodes in order to broaden the range of nematodes against which the agent(s) is/are effective.

The invention will now be explained with the help of following examples. However, the scope of the invention should not be limited to these examples as the person skilled in the art can easily vary the proportion of the ingredients and combinations.

Example 9: In Silico Identification of flp-14 Gene

Nematode genome data base and also the genomic information of M. incognita was used for in silico analysis and identification of flp-14 gene, an FMRFamide like peptide, as a potential gene target to disrupt various activities in the life cycle of M. incognita which could lead to the disruption of parasitic activities.

Example 10: Bioefficacy of $T_1$ Tobacco Lines Against M. incognita

Figure 7:
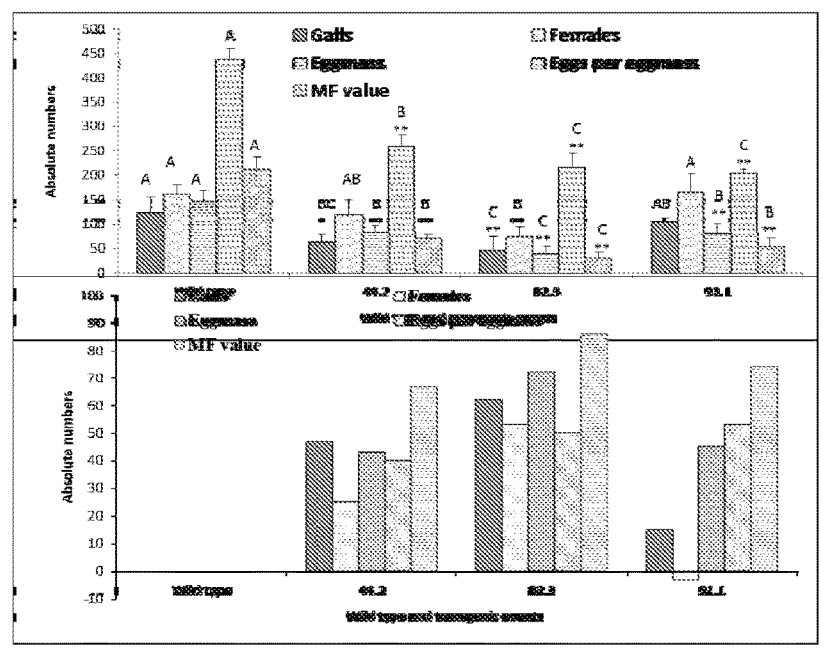
Figure 8:
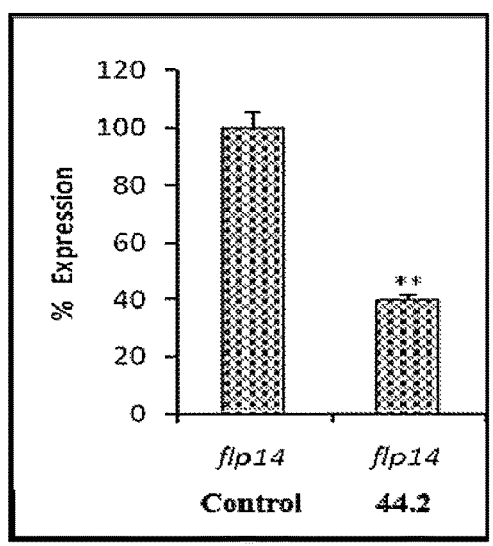

Nematode bioassays were performed in order to study the resistance offered against M. incognita by inoculating freshly hatched J2s on $T_1$ generation plants that were confirmed for the flp-14 integration and expression of dsRNA. The plants were harvested 30 days after inoculation and observations were recorded on various parameters to determine the effect of host delivered RNAi on nematode infection, development and reproduction. $T_1$ plants of the three selected independent events were screened in case of flp-14 and the nematode infection was scored in terms of number of galls, females, egg masses and eggs per egg mass produced in each plant (FIGS. 7 & 8). It was quite evident that host delivered RNAi silencing of both the target genes resulted in reduced root galling due to the nematode infection and there was an increased root growth in the transgenics compared to the wild type plants. Silencing of flp-14 generally reduced the nematode infection as indicated by reduction in the number of galls (Table 4). Correspondingly, there was a reduction in number of females and the percentage reduction ranged between 50-103% in flp-14 RNAi plants compared to the wild type plants (FIG. 8). Interestingly, not all the females in these roots could reproduce since the percentage reduction of egg masses ranged from 28 to 57% which indicated that only 50% of the females could reproduce (FIG. 7). Likewise, silencing of flp-14 had also reduced the fecundity of the nematodes as percentage reduction in number of eggs per egg mass ranged from 47-50% (FIG. 7). Finally, the nematode MF reflecting the overall ability of the nematode to be a successful parasite was reduced by about 61 to 78% due to the silencing of flp-14.

An interesting corroboration with the bioefficacy was observed by qRT-PCR quantification of flp-14 (FIG. 8) in the females extracted from the transgenic tobacco plants harboring the respective genes. The observation showed down regulation of the genes suggesting effective host delivered RNAi in the transgenic plants. Target specific host delivered gene silencing could also be established as in case of in vitro RNAi silencing.

We claim:

1. A process for controlling the multiplication index of a root knot nematode by reducing the number of reproducing population and number of progeny per individual, said process essentially comprises steps of transforming said host plant cell with a nucleic acid, which express to produce a transcript that forms a double stranded RNA having a SEQ ID No. 1 and the complement thereof and consequently facilitates the inhibition of the expression of mRNA of a target gene or a segment thereof present in said nematode species, wherein said target gene is FMRFamide-like peptides 14 gene or flp-14 gene of said nematode and wherein said process causes reduction of about 78% of the multiplication index of said nematode in the transformed host plant cell as compared to the control population of host cell.

2. The process as claimed in claim 1, wherein said nematode is *Meloidogyne incognita*.

3. The process as claimed in claim 1, wherein said plant is from Solanaceous family.

4. The process as claimed in claim 1, wherein said plant is *Nicotiana tabaccum* or *Solanum melongena*.

5. The process as claimed in claim 1, wherein said process reduces about 41% of the female population laying eggs as compared to the control population.

6. The process as claimed in claim 1, wherein said process reduces about 48% in the eggs per egg mass as compared to the control population.

7. The process as claimed in claim 1, wherein said process reduces about 57% in the eggs as compared to the control population.

8. The process as claimed in claim 1, wherein Critical Difference value for the reduction in multiplication index of said nematode is about 1.91.

9. The process as claimed in claim 1, wherein Critical Difference value for the reduction in number of egg per egg mass of said nematode is about 1.27.

10. The process as claimed in claim 1, wherein Critical Difference value for the reduction in number of egg mass per plant of said nematode is about 1.65.

11. The process as claimed in claim 1, wherein Critical Difference value for the reduction in number of female population is about 1.83.

12. The process as claimed in claim 1, wherein Critical Difference value for the reduction in number of galls is about 1.26.

13. A method of transferring a RNAi vector for gene silencing of flp-14 gene of root knot nematodes in host plants for control of root-knot nematodes, said method comprising steps of:
   (a) preparing the RNAi vector construct comprising SEQ ID No. 1 and the complement thereof;
   (b) transferring the vector of step (a) into an *Agrobacterium* strain;
   (c) infecting the host explants with *Agrobacterium* of step (b); and
   (d) obtaining the transformed host plants.

14. A method of expressing dsRNA transcript for RNAi or gene-silencing of flp-14 gene for controlling root-knot nematodes infection, said method comprising steps of:
   (a) preparing an expression vector comprising SEQ ID No.1 and the complement thereof;
   (b) transferring the vector of step (a) in a host plant;
   (c) obtaining the expression of in vitro and in vivo transcript of dsRNA.

15. Transgenic plants expressing double stranded RNA having SEQ ID No.1 and the complement thereof for controlling infection of root-knot nematodes by RNAi or gene silencing of flp-14 gene of root-knot nematodes.

* * * * *